United States Patent [19]
Akita et al.

[11] Patent Number: 5,952,582
[45] Date of Patent: Sep. 14, 1999

[54] TEST APPARATUS WITH CONTROL CONSTANT COMPUTING DEVICE

[75] Inventors: Noritaka Akita, Hatano; Kohji Inoue; Yoshikazu Yasuda, both of Kyoto, all of Japan

[73] Assignee: Shimadzu Corporation, Kyoto, Japan

[21] Appl. No.: 08/991,564

[22] Filed: Dec. 16, 1997

[30] Foreign Application Priority Data

Dec. 27, 1996 [JP] Japan .................................. 8-350355

[51] Int. Cl.⁶ .............................. G01L 1/00; G01N 3/00
[52] U.S. Cl. ................................................. 73/855; 73/805
[58] Field of Search ............................ 73/781, 788, 805, 73/855, 856, 846

[56] References Cited

U.S. PATENT DOCUMENTS

| | | | |
|---|---|---|---|
| 5,103,671 | 4/1992 | Dyvig | 73/168 |
| 5,327,790 | 7/1994 | Levin et al. | 73/862.321 |
| 5,511,431 | 4/1996 | Hinton | 73/806 |
| 5,712,431 | 1/1998 | Vilendrer | 73/846 |
| 5,844,140 | 12/1998 | Seale | 73/633 |

*Primary Examiner*—Max Noori
*Attorney, Agent, or Firm*—Kanesaka & Takeuchi

[57] ABSTRACT

A test apparatus is formed of an error area computing device, an upper limit value computing portion and a delay time computing portion. The error area computing device computes an error area corresponding to a difference between waves of a request signal and an output signal to thereby correct control constants for a PID controller based on the error area. The upper limit value computing portion prevents the control constants from being corrected at values higher than upper limit values, and the delay time computing portion computes a phase delay time between the request signal and the output signal. In case the request signal has a higher frequency, the error area is computed as a value from which an error area due to the phase delay time is deducted. Thus, in the test apparatus, the control constants of the PID controller can be optimized for every cycle of an input signal, i.e. the request signal, and in the process of optimizing of the control constants, a bad influence is not exerted to a specimen.

8 Claims, 4 Drawing Sheets

TEST APPARATUS WITH CONTROL CONSTANT COMPUTING DEVICE

BACKGROUND OF THE INVENTION AND RELATED ART STATEMENT

The present invention relates to a test apparatus for determining control constants of a PID controller by an autotuning or automatic tuning method.

Heretofore, as a fatigue test machine wherein loads, such as tensile load and compressive load, are continuously applied to a specimen or test piece for a long time to thereby test a fatigue strength of the specimen, there has been known a test machine wherein an actuator for applying loads to the specimen is controlled by a PID controller through a feedback so that waves of displacement of the specimen or waves of the loads applied to the specimen, i.e. waves of an output signal, coincide with waves of a request signal, i.e. input signal, inputted at a predetermined cycle.

In the fatigue test machine, although control constants, such as proportional gain K, integral time TI and derivative time TD, of the PID control are fixed, the control constants are set to sufficiently small values so that the output signal is not unstabilized by changes of conditions of a system, such as changes of characteristics of the specimen and changes of circumferential conditions; more specifically, for example, hunting does not occur in output waves even in case rigidity of the specimen is changed by the loads during the test.

However, as described above, if the control constants of the PID control are simply set to the small values, response degree of the output waves is deteriorated especially in a high frequency area, and line forming ability of the output signal against the input signal is deteriorated. Therefore, there is carried out a control method, i.e. autotuning method, for changing the control constants of the PID control based on the changes of conditions of the system during the test.

In the autotuning method, there is employed a control method wherein, for example, a parameter for showing conditions of the system is determined by sampling data of output signals with respect to input signals over a plurality of cycles during a test, and the control constants of the PID control are changed based on a theoretical equation from the parameter. However, in the control method, samplings of the data over the plural cycles are required, which takes a long time and is not suitable for the fatigue test.

Also, as another example of the autotuning method, there has been known, so called, a noise method. In the noise method, instead of sampling data over the plural cycles, a noise component is intentionally added to an input signal, and a parameter for showing conditions of a system is determined according to a response with respect to the noise component. The noise method is superior in that the parameter is determined for every cycle. However, since the noise component contained in the input signal acts as a load suddenly applied to the specimen, a bad influence may be exerted to the specimen. This becomes a problem especially when a noise strength is increased in order to improve accuracy of parameter determination.

The present invention has been made in view of the above described defects, and an object of the invention is to provide a test apparatus, wherein control constants of a PID control can be optimized for every cycle.

Another object of the invention is to provide a test apparatus as stated above, wherein a bad influence is not exerted to a specimen in the optimizing course of the control constants.

Further objects and advantages of the invention will be apparent from the following description of the invention.

SUMMARY OF THE INVENTION

According to a first aspect of the invention, a test apparatus is formed of an actuator for applying loads to a specimen, and a PID controller for controlling the actuator through feedback so that an output signal indicating a detected condition of a load applied to the specimen coincides with a request signal. The test apparatus further includes an error area computing device for computing, as an error area, a quantity corresponding to an integral value of a difference between the output signal and the request signal over a predetermined error calculating time, and a control constant computing device for correcting the control constants of the PID controller based on the error area.

According to a second aspect of the present invention, when the request signal has a frequency higher than a predetermined frequency, the error area computing device computes only a difference, as the error area, between signal waves themselves of the output signal and the request signal by removing a portion due to a phase delay from the error area.

According to a third aspect of the present invention, a test apparatus is formed of an actuator for applying loads to a specimen; a PID controller for controlling the actuator through feedback so that an output signal indicating a detected condition of a load applied to the specimen coincides with a request signal, and a control constant computing device for correcting control constants of the PID controller. The respective control constants of the PID controller are provided with upper limit values, and when any one of corrected values of the respective control constants calculated by the control constants computing device is larger than the upper limit value corresponding thereto, the control constant of the PID controller is corrected to the corresponding upper limit value.

According to a fourth aspect of the invention, an upper limit value computing device includes a database for storing the upper limit values of the respective control constants corresponding to respective frequencies of the request signals.

DETAILED DESCRIPTION OF PREFERRED EMBODIMENTS

Hereunder, referring to the accompanying drawings, an embodiment of the present invention is described.

Figure 1:
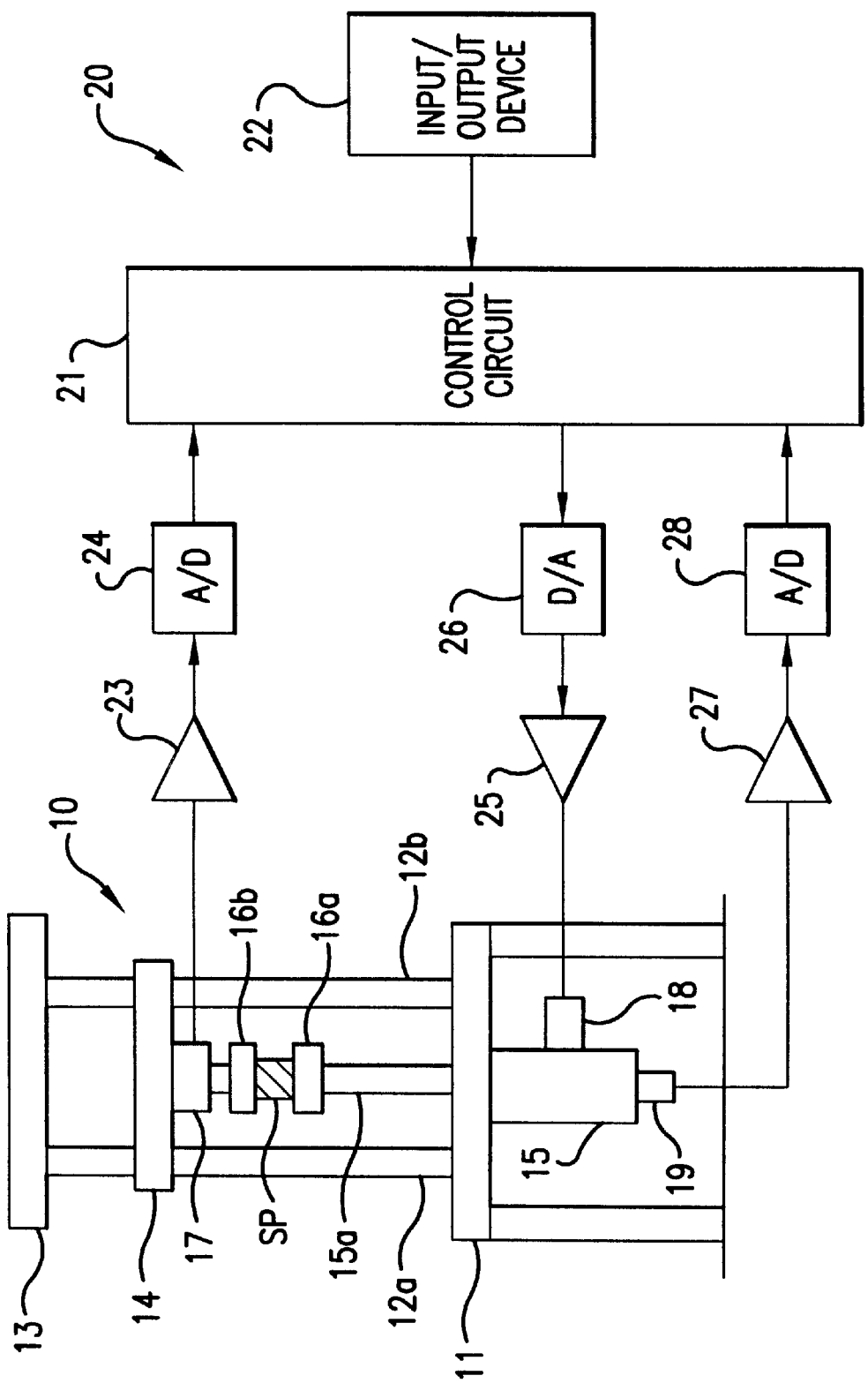
FIG. 1 is a schematic view for showing a whole structure of a test apparatus of an embodiment according to the invention.

FIG. 1 shows a whole structure of a test apparatus according to the present invention. As shown in the drawing, a load frame formed of a pair of columns 12a, 12b and a yoke 13 is provided on a base 11 of a main portion 10 in the test apparatus for applying a compressive load or tensile load to a specimen SP, and a vertically movable crosshead 14 is attached to the columns 12a, 12b.

A hydraulic actuator 15 for generating a load is installed under the base 11, and an upper end of a piston rod 15a extending upward therefrom is provided with a lower jig 16a for fixing the specimen SP. On the other hand, an upper jig 16b for fixing the specimen SP through a load cell 17 is provided under the crosshead 14 fixed to a predetermined height according to a size of the specimen SP. Thus, the specimen SP is held between the upper jig 16b and the lower jig 16a.

Under the state, when the piston rod 15a of the hydraulic actuator 15 is extended and withdrawn, a load is repeatedly applied to the specimen SP. Incidentally, the extension and withdrawal movements of the hydraulic actuator 15 are controlled by adjusting a direction and amount of a compressed oil to the hydraulic actuator 15 through a servo valve 18. Also, a stroke of the hydraulic actuator 15, i.e. a displacement of the specimen SP, can be detected by an actuation transformer 19 provided under the hydraulic actuator 15.

A control system 20 for controlling the test apparatus main portion 10 includes a control circuit 21 formed of a microcomputer and peripheral parts thereof. Inputted to the control circuit 21 from an input/output device 22 is a request signal, i.e. input signal, with respect to the stroke of the hydraulic actuator 15, i.e. displacement of the specimen SP, or a duty, i.e. load, itself applied to the specimen SP. As the request signal, for example, there are a triangular wave and a sine wave having a predetermined cycle. Further, inputted to the control circuit 21 are a detected signal of the load applied to the specimen SP from the load cell 17 through an amplifier 23 and an A/D converter 24, and a detected signal of the stroke of the hydraulic actuator 15 from the actuating transformer 19 through an amplifier 27 and an A/D converter 28, respectively. Based on these signals, the control circuit 21 outputs an operating signal to the servo valve 18 through a D/A converter 26 and an amplifier 25 to thereby control movements of the hydraulic actuator 15.

Figure 2:
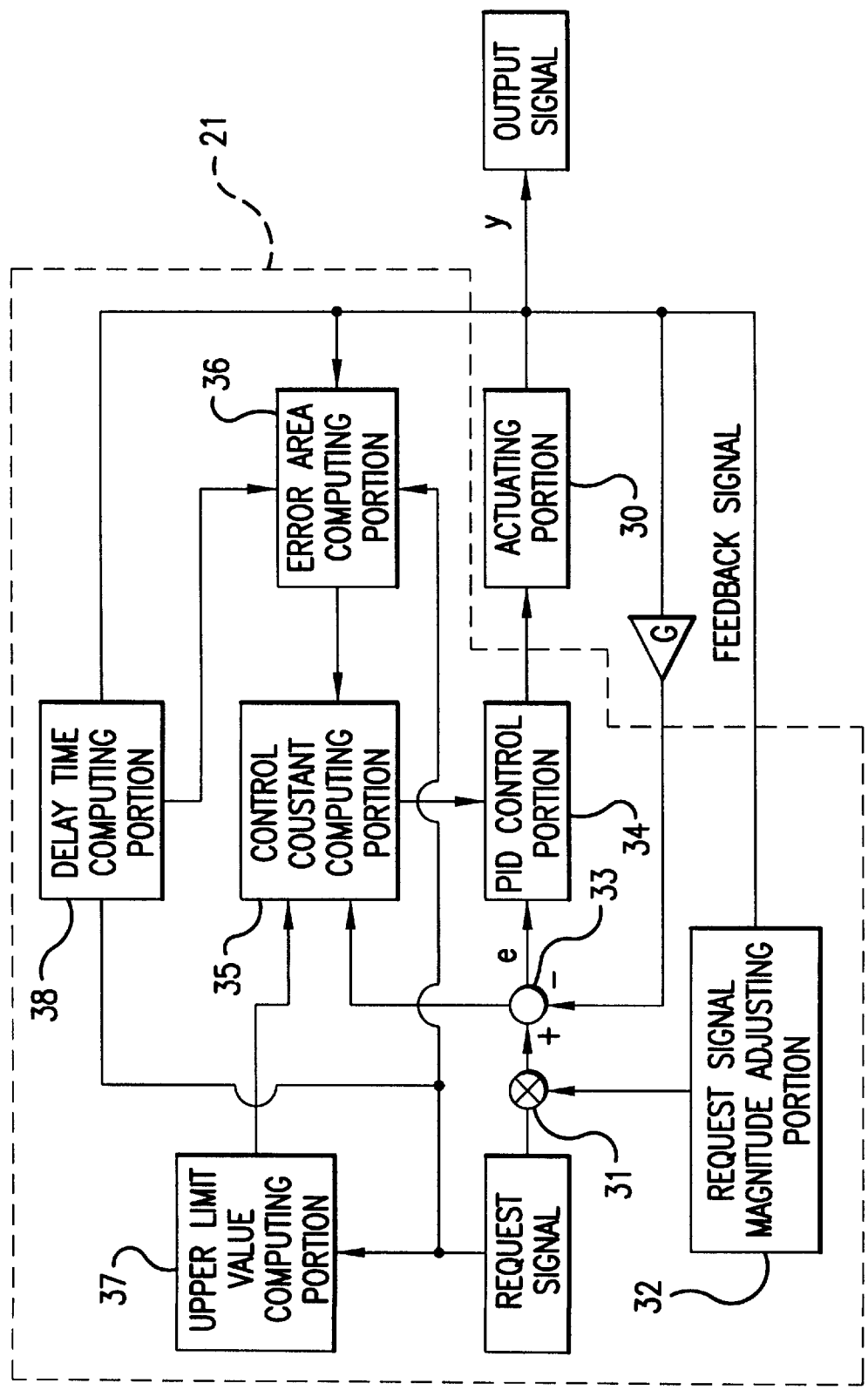
FIG. 2 is a block diagram for showing a control system of the embodiment according to the invention.

FIG. 2 is a block diagram for showing processing contents in the control circuit 21. As shown in the drawing, after the request signal inputted from the input/output device is multiplied at an adder 31 by a coefficient calculated by a request signal magnitude control device 32 according to an output signal from an actuating portion 30 to thereby adjust a magnitude, the adjusted request signal is inputted into an adder 33. The adder 33 inputs into a PID controller 34 a deflection between the magnitude adjusted request signal and a feedback signal of the output signal. The PID controller 34 outputs an operating signal to the actuating portion 30 and controls the actuating portion 30 through feedback so that an output signal from the actuating portion 30 coincides with the request signal.

Incidentally, the actuating portion 30 includes the hydraulic actuator 15, servo valve 18, specimen SP and load cell 17, as shown in FIG. 1. As to whether the request signal is for the stroke of the hydraulic actuator 15, i.e. displacement of the specimen SP, or for a load applied to the specimen SP, the output signal is selected from either the detected signal for the stroke of the hydraulic actuator 15, i.e. displacement of the specimen SP, or the detected signal for the load applied to the specimen SP.

Also, the control circuit 21 includes a control constant computing portion 35 for computing control constants, such as a proportional gain K, integral time TI and derivative time TD, of the PID controller 34, and also includes an error area computing portion 36, upper limit value computing portion 37 and delay time computing portion 38 which characterize the present invention. The respective control constants of the PID controller 34 are replaced with corrected values computed by the control constant computing portion 35 during a fatigue test so that the respective control constants are optimized.

Incidentally, a control computing equation is generally expressed by using the proportional gain K, integral time TI and derivative time TD as follows:

$$y=k(e+1/T_1 \int e\,dt+T_D\, de/dt) \quad (1)$$

wherein y represents an operating variable which corresponds to the output signal of the present embodiment; and e represents a deflection which corresponds to the deflection between the output signal and the magnitude adjusted request signal after it has been adjusted by the request signal magnitude control portion 32 of the present embodiment.

Figure 3:
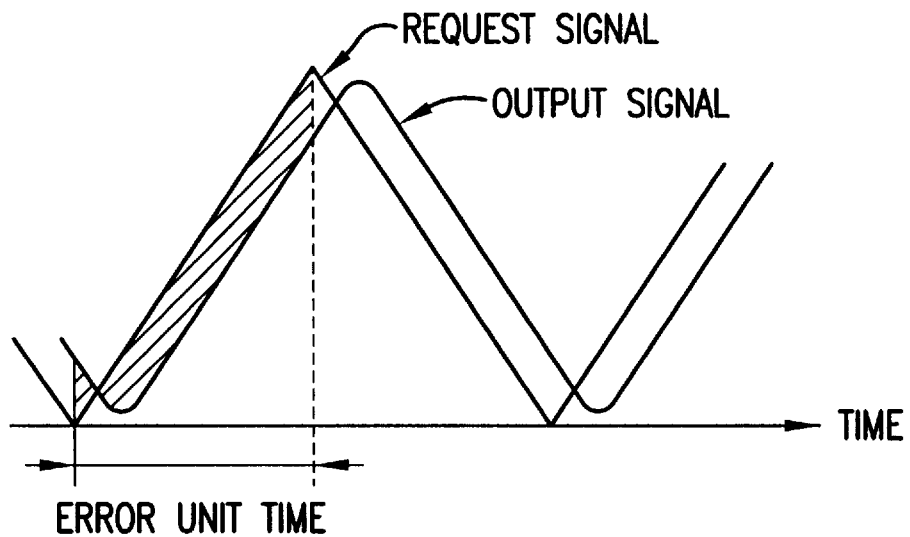
FIG. 3 is a characteristic graph for showing a request signal, an output signal and an error area therebetween of the embodiment according to the invention.

The error area computing portion 36 calculates an error degree between the request signal and the output signal as an error area α. As shown in FIG. 3, the error area α corresponds to a value obtained by integrating an absolute value of a difference between the request signal and the output signal over a predetermined error calculating unit time, for example, a half cycle of the request signal. In other words, in a characteristic graph for showing time changes of the request signal and the output signal as shown in FIG. 3, an area, shown by oblique lines in FIG. 3, surrounded by the request signal and the output signal during the error calculating unit time corresponds to the error area α.

The error area α thus obtained is inputted into the control constant computing portion 35 which corrects the respective control constants of the PID controller based on the error area α. Hereinafter, the method for correcting the constants of the PID controller is referred to as "error area minimizing method". More specifically, for example, with respect to the present proportional gain K, integral time TI and derivative time TD, the corrected proportional gain K', integral time TI' and derivative time TD' are expressed as follows:

$$K'=K(1+\alpha) \quad (2)$$

$$TI'=TI(1+\alpha) \quad (3)$$

$$TD'=TD(1+\alpha) \quad (4).$$

Incidentally, the corrections of the control constants can be carried out from the cycle next to a cycle where an error area α is sampled, and the control constants are optimized whenever one cycle is performed. More specifically, as in the present embodiment, in case the error computing time for computing the error area is less than one cycle of the request signal, calculation of the error area can be carried out within the one cycle, and corrections of the control constants can be continuously carried out for each cycle.

As described above, by multiplying the proportional gain K, integral time TI and derivative time TD by (1+α), a response degree of the output signal with respect to the request signal, i.e. input signal, can be increased, so that the respective control constants with respect to conditional changes of a system, such as changes of characteristics of a specimen and circumferential conditions, can be optimized; and the output signal can be automatically adjusted to correctly follow the request signal. Incidentally, in the error area minimizing method, it has been confirmed that, for example, in case the request signal, i.e. input signal, is a lamp signal, linearity or linear condition of the output signal can be improved by about 20% by a simulation calculation when compared with the linearity before the error area minimizing method is applied.

The upper limit value computing portion 37 computes upper limit values, i.e. an upper limit value KL of the proportional gain, upper limit value TIL of the integral time and upper limit value TDL of the derivative time, of the respective control constants, such as the proportional gain K, integral time TI and derivative time TD, of the PID controller according to a frequency of the request signal. Incidentally, the upper limit values or limit values of the respective control constants are stored in a database based on the frequency of each request signal.

The thus computed limit values of the respective control constants are inputted into the control constant computing portion 35 in which, for example, the respective control constants corrected by the error area minimizing method are compared with the limit values corresponding thereto. When the corrected values of the respective control constants are less than the limit values, the corrected values are set as the control constants of the PID controller 34. On the other hand, if any one of the corrected values, i.e. corrected value K' of the proportional gain, corrected value TI' of the integral time or corrected value TD' of the derivative time, of the control constants is larger than the limit value corresponding thereto, the corrected value larger than the limit value is not adopted, and the upper limit value corresponding thereto, i.e. limit value KL, limit value TIL or limit value TDL, can be set as a control constant of the PID controller 34.

As described hereinabove, by setting the upper limit values to the respective control constants of the PID controller, it is possible to prevent huntings from being created to the output signal due to too large control constants. Particularly, when corrections of the control constants are carried out by the error area minimizing method, in case a hunting is created because of too large control constants, especially too large proportional gain K, the hunting portion is also added up as an error area $\alpha$, so that the control constants are further increased by the error area $\alpha$ including the hunting portion to thereby induce huntings more and more, which may result in a vicious circle. In the invention, since the limit values are set to the respective control constants, the control constants can be corrected in an area without being caught by the vicious circle.

The delay time computing portion 38 compares a request signal from the input/output device 22 and an output signal from the actuating portion 30 to calculate a delay time, i.e. phase delay, of the output signal with respect to the request signal. More specifically, for example, when the request signal is triangular waves or sine waves, a time difference from a peak value of the request signal to a peak value of the output signal is calculated, and the time difference is used as the delay time.

The thus obtained delay time is taken into the error area computing portion 36. Then, only in case the request signal has a high frequency greater than a predetermined frequency, the error area computing portion 36 executes calculation of the error area $\alpha$ only after the output signal is brought close to a side of the request signal by the delay time, so that the error area $\alpha$ does not include an error area due to the delay time. More specifically, when the error area $\alpha$ is computed, in a state where a peak value of the request signal is adjusted to coincide with a peak value of the output signal, error portions of these waves themselves, i.e. deformed portions of the waves of the output signal, are used as the error area $\alpha$.

Figure 4:
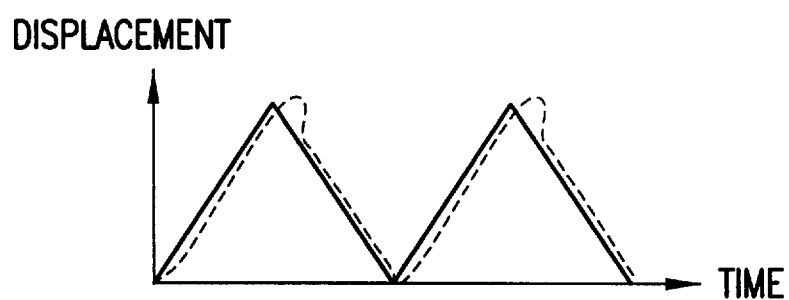
FIG. 4 is a characteristic graph for showing a relationship between the request signal and the output signal of the embodiment according to the invention.
Figure 5:
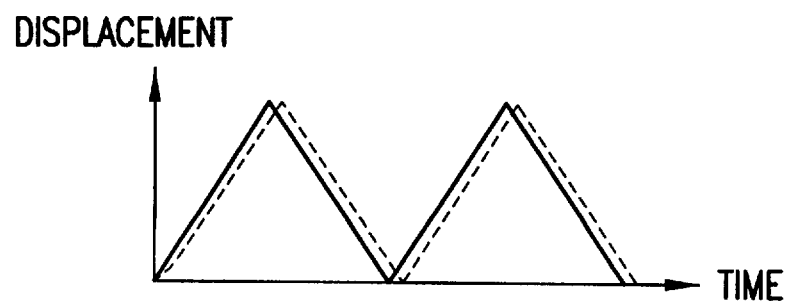
FIG. 5 is a characteristic graph for showing a relationship between the request signal and the output signal of the embodiment according to the invention.

Here, an explanation is made as to why the error area in case the request signal is a high frequency is the error area $\alpha$ excluding the portion corresponding to the delay time. Generally, when the request signal is a high frequency, the output signal is forced to follow the request signal by autotuning so that delay of the output signal with respect to the request signal is not made. As a result, as shown in FIG. 4, distortions are formed in the waves of the output signal shown by broken lines with respect to the request signal, i.e. input signal, shown by solid lines. Therefore, in the present invention, when the request signal is the high frequency, calculation of the error area $\alpha$ is carried out by subtracting the error area due to the delay time. Thus, as shown in FIG. 5, while admitting that there is the delay time, the waves of the output signal shown by the broken lines are controlled to coincide with the waves of the request signal shown by the solid lines. Incidentally, when the request signal is a low frequency signal, the delay time can be almost neglected. Therefore, it is not necessary to subtract the portion corresponding to the delay time from the error area $\alpha$ as in the case of the high frequency, so that the error area $\alpha$ can be computed as they are.

Figure 6:
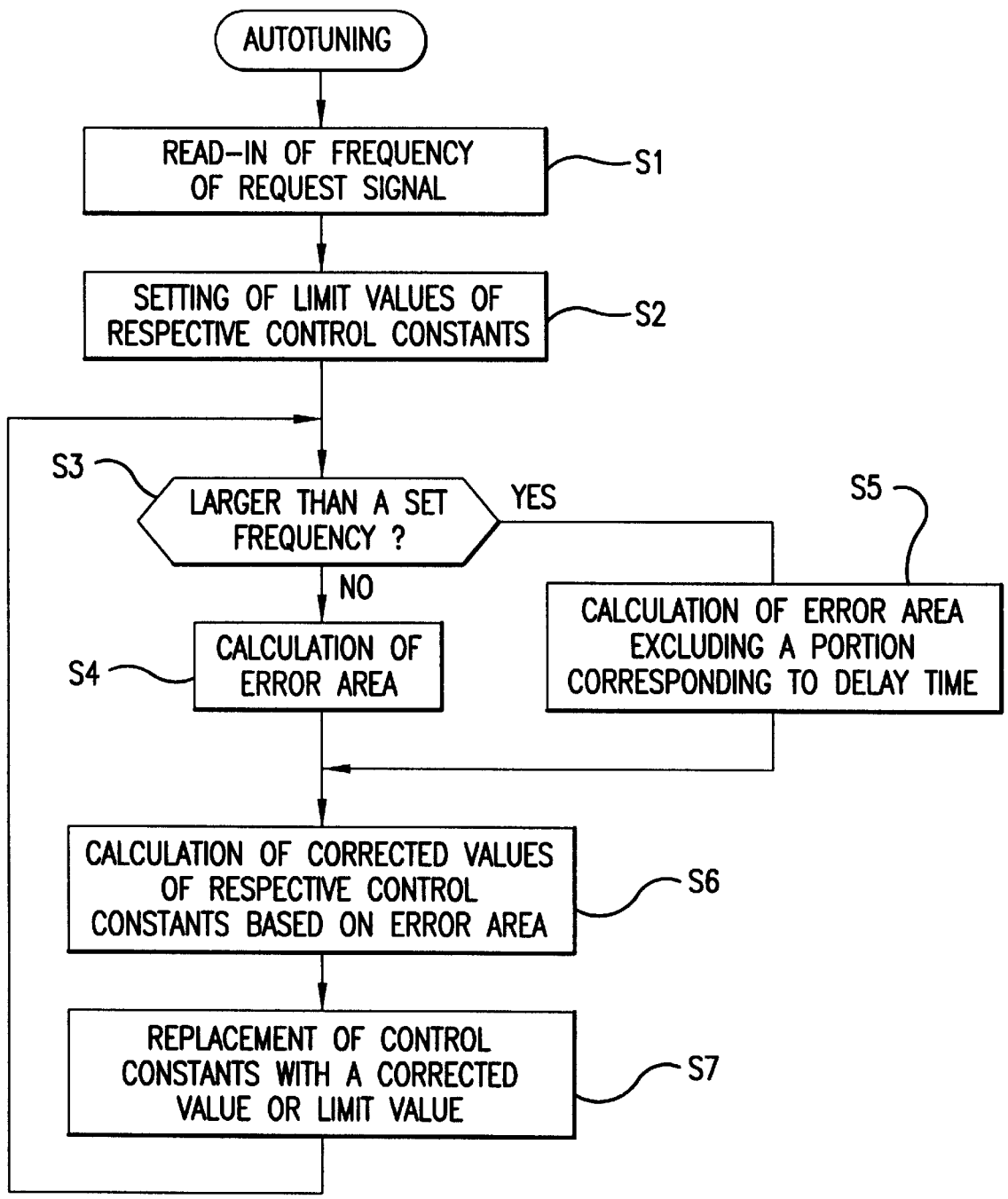
FIG. 6 is a flow chart for showing a procedure in a control circuit of the embodiment according to the invention.

Next, an autotuning or automatic tuning process according to the present invention is described with reference to a flow chart shown in FIG. 6.

In the test apparatus of the invention, when autotuning of the respective control constants of the PID controller starts, a frequency of a request signal is read in the control circuit 21 at step S1.

At step S2, according to a relationship between the frequency of the request signal and upper limit values of the respective control constants, which have been incorporated in a database beforehand, the respective upper limit values, such as limit value KL of the proportional gain, limit value TIL of the integral time and limit time TDL of the derivative time, with respect to the respective control constants, such as proportional gain K, integral time TI and derivative time TD, are determined by the upper limit value computing portion 37.

At step S3, it is determined whether the frequency of the request signal is higher than a predetermined frequency or not. In case the frequency of the request signal is lower than the predetermined frequency, the processing proceeds to step S4, wherein an error area $\alpha$ between the request signal and the output signal is computed by the error area computing portion 36, and the processing proceeds to step S6.

On the other hand, in case it is determined at step S3 that the frequency of the request signal is higher than the predetermined frequency, the processing proceeds to step S5, wherein by the error area computing portion 36, the error area $\alpha$ is computed after waves of the output signal are shifted, on a time axis, by a portion corresponding to a delay time of the output signal with respect to the request signal, and the processing proceeds to step S6.

At step S6, based on the thus obtained error area $\alpha$, corrected values, such as corrected value K' of the proportional gain, corrected value TI' of the integral time and corrected value TD' of the derivative time, of the respective control constants are computed by the control constant computing portion 35.

At step S7, the thus corrected values of the respective control constants are compared with the limit values of the respective control constants determined at step S2. In case the corrected values of the control constants are smaller than the limit values corresponding thereto, the corrected values are replaced by control constants of the PID controller 34. On the other hand, if there is the corrected value of the control constant larger than the limit value corresponding thereto, the control constant of the PID controller 24 is replaced by the limit value corresponding thereto.

As described hereinabove, a loop for correcting the respective control constants from step S3 to step S7 is repeated during a fatigue test. However, when the request signal is changed, step S1 and step S2 are executed. The control constants of the PID controller are continuously automatically optimized according to characteristic changes and changes of circumferential conditions of a specimen.

Incidentally, in the above embodiment, corrections of the respective control constants of the PID controller based on the error area α were carried out by multiplying of (1+α) as shown by equations (2)–(4). However, the corrections of the control constants based on the error area α are not limited to the above described method. For example, with respect to the present proportional gain K, integral time TI and derivative time TD, corrected proportional gain K', corrected integral time TI' and corrected derivative time TD' may be set as follows:

$$K'=K(1+\alpha) \quad (5)$$

$$TI'=TI(1-kd\cdot\alpha) \quad (6)$$

$$TD'=TD(1-ki\cdot\alpha) \quad (7)$$

wherein kd and ki in equations (6) and (7) represent coefficients determined through experiences. The kd and ki are, for example, expressed as follows:

$$kd=k\cdot(1+P\cdot Tterm)$$

$$ki=k\cdot(1-P\cdot Tterm)$$

wherein k represents an error coefficient, P represents a periodic coefficient and Tterm represents a periodic time. The periodic time Tterm is set to be a small value when the request signal, i.e. input signal, is a high frequency, so that the integral time TI is made small and the derivative time TD is made large. Also, the periodic time Tterm is set to be a large value when the request signal, i.e. input signal, is a low frequency, so that the integral time TI is made large and the derivative time TD is made small. As described above, by experimentally correcting a coefficient to be multiplied by each control constant, the respective control constants can be more properly optimized by the error area minimizing method.

Incidentally, in the above embodiment, the upper limit values of the control constants set by the upper limit value computing portion 37 are applied to the error area minimizing method. However, the control method for setting the upper limit values of the control constants can be also applied to various autotunings for the control constants other than the error area minimizing method.

According to the present invention, the control constants of the PID controller are corrected based on the request signal corrected according to the error area showing a magnitude of the shift of the output signal, for example, as the error area becomes large the proportional gain becomes large. Thus, the control constants of the PID controller are properly optimized; the request signal quickly follows the output signal; and a specimen SP can be continuously provided with desired loads.

Also, when the request signal has a frequency higher than a predetermined frequency, the error area is calculated as a difference of waves themselves of the request signal and the output signal. Therefore, the output signal can be controlled to waves which are proper reproductions of the request signal although there is a time delay without distorting the output signal by forcibly following the output signal to the request signal having the high frequency.

Further, according to the present invention, since the control constants of the PID controller have the upper limit values, respectively, it is possible to prevent huntings from being created in the output signal due to too large control constants. Especially, in case a control constant is corrected based on an error area, when the control constant, particularly the proportional gain, is made too large so that a hunting is created, the hunting portion is also added to the error area. As a result, the control constant is further increased, and the hunting occurs more often, which may result in a vicious circle. However, in the present invention, this can be effectively prevented.

Also, if the upper limit values of the control constants and frequencies of the request signals are incorporated in a database, proper limit values for every frequencies can be easily set.

While the invention has been explained with reference to the specific embodiments of the invention, the explanation is illustrative, and the invention is limited only by the appended claims.

What is claimed is:

1. A test apparatus comprising:
   an actuator for applying a load to a specimen;
   a PID controller connected to the actuator, said PID controller controlling the actuator through feedback so that an output signal indicating a condition of the load applied to the specimen coincides with a request signal for actuating the actuator;
   an error area computing device for computing, as an error area, a quantity corresponding to an integral value of a difference between the output signal and the request signal over a predetermined error computing time; and
   a control constant computing device connected to the PID controller and the error area computing device, said control constant computing device calculating control constants for the PID controller continuously based on the error area and always correcting control constants of the PID controller to optimum control constants based on the calculated control constants.

2. A test apparatus according to claim 1, wherein said error area computing device calculates such that when the request signal is a high frequency higher than a predetermined frequency, only a difference between signal waves of the output signal and the request signal is calculated as the error area by removing a portion due to a phase delay from the error area.

3. A test apparatus according to claim 2, further comprising a delay time computing portion connected to the error area computing device, said delay time computing portion comparing the request signal and the output signal to calculate the phase delay of the output signal with respect to the request signal.

4. A test apparatus according to claim 1, wherein said predetermined error computing time is less than one cycle of the request signal so that the control constants of the PID controller is optimized for every cycle.

5. A test apparatus according to claim 1, further comprising a limit value computing device connected to the control constant computing device, said limit value computing device providing upper limit values for the respective control constants of the PID controller, said control constant computing device operating such that when one of corrected values of the control constants is larger than the limit value corresponding thereto, the control constant for the PID controller is corrected to the corresponding limit value and supplied to the PID controller.

6. A test apparatus comprising:

an actuator for applying a load to a specimen;

a PID controller connected to the actuator, said PID controller controlling the actuator through feedback so that an output signal indicating a condition of the load applied to the specimen coincides with a request signal for actuating the actuator;

a control constant computing device connected to the PID controller for correcting control constants of the PID controller; and an upper limit value computing device connected to the control constant computing device, said upper limit value computing device providing upper limit values for the respective control constants of the PID controller in each frequency of the request signal, said control constant computing device operating such that when one of corrected values of the control constants is larger than the upper limit value corresponding thereto, the control constant for the PID controller is corrected to the corresponding upper limit value and supplied to the PID controller.

7. A test apparatus according to claim 6, wherein said upper limit value computing device includes a database for storing the upper limit values of the respective control constants corresponding to said each frequency of the request signal.

8. A test apparatus according to claim 1, wherein said predetermined error computing time by the error area computing device is less than one cycle of the request signal to thereby correct the control constants of the PID controller in every cycle.

* * * * *